United States Patent [19]

Wigness et al.

[11] Patent Number: 5,120,312
[45] Date of Patent: Jun. 9, 1992

[54] METHOD AND APPARATUS FOR CATHETERIZATION

[75] Inventors: Bruce D. Wigness; Frank D. Dorman, both of Minneapolis, Minn.

[73] Assignee: Regents of the University of Minnesota, Minneapolis, Minn.

[21] Appl. No.: 511,562

[22] Filed: Apr. 20, 1990

[51] Int. Cl.⁵ .............................................. A61M 5/00
[52] U.S. Cl. ...................................... 604/175; 604/93
[58] Field of Search ............................ 604/51, 175, 93

[56] References Cited

U.S. PATENT DOCUMENTS

| | | | |
|---|---|---|---|
| 3,333,588 | 8/1967 | Schulte | 604/175 |
| 3,590,451 | 11/1970 | Zeman | 604/175 |
| 4,315,513 | 2/1982 | Nawash et al. | 604/175 |
| 4,673,394 | 6/1987 | Fenton, Jr. | 604/175 |
| 4,676,782 | 6/1987 | Yamamoto et al. | 604/175 |
| 4,718,893 | 1/1988 | Dorman et al. | 604/67 |
| 4,722,261 | 9/1988 | Von Hoff | 604/175 |
| 4,772,263 | 9/1988 | Dorman et al. | 604/132 |
| 4,772,270 | 9/1988 | Wiita et al. | 604/175 |
| 4,781,693 | 11/1988 | Martinez et al. | 604/175 |
| 4,861,341 | 8/1989 | Woodburn | 604/175 |
| 4,886,502 | 12/1989 | Poirer et al. | 604/175 |
| 4,903,707 | 2/1990 | Knute et al. | 604/175 |
| 4,903,707 | 2/1990 | Knute et al. | 604/175 |
| 4,986,810 | 1/1991 | Semrad | 604/175 |

OTHER PUBLICATIONS

R. F. Kyle et al., *The Journal of Bone and Joint Surgery, Incorporated*, 62-A, 1308–1314 (Dec. 1980).
O. Namiki et al., *International Journal of Clinical Pharmacology, Therapy, and Toxicology*, 20, 501–507 (1982).
J. Raveh et al., *J. Oral Maxillofac. Surg.*, 42, 281–294 (1984).
E. Morscher et al., *Arch. Orthop. Trauma Surg.*, 103, 175–178 (1984).
L. B. Dahl et al., *Annals of the Rheumatic Diseases*, 44, 817–822 (1985).
D. Amiel et al., *Clinical Orthopaedics and Related Research*, 306–311 (Jun. 1985).
A. Bragantini et al., *Clinical Trials Journal*, 24, 333–340 (1987).
T. Iizuka et al., *J. Cranio-Max.-Fac. Surg.*, 15, 24–27 (1987).
J. Raveh et al., *The Otolaryngologic Clinics of North America*, 20, 535–558 (Aug. 1987).
J. R. Russell et al., *British Journal of Oral and Maxillofacial Surgery*, 25, 83–85 (1987).
G. Leardini et al., *Clinical Trials Journal*, 24, 341–350 (1987).
G. Grecomoro et al., *Pharmatherapeutica*, 5, 137–141 (1987).
H. Buchwald et al., *Implantable Pumps. ASAIO Primers*, No. 2, J. B. Lippincott Co., Philadelphia (1987), pp. 1–96.
T. D. Rohde et al., "Implantable Infusion Pumps" in *Drug Delivery Devices*; P. Tyle, ed.; Marcel Dekker, Inc., New York; 235–260 (1988).
S. Hellem et al., *J. Cranio-Max.-Fac. Surg.*, 16, 173–183 (1988).
P. Cuevas et al., *Biochemical and Biophysical Research Communications*, 156, 611–618 (1988).
T. D. Sisk, "General Principles of Fracture Treatment" in *Campbell's Operative Orthopaedics*, 7th Edition, vol. 3, A. H. Crenshaw, ed.; C. V. Mosby Co., St. Louis; 1561–1576 (1987).

*Primary Examiner*—Paul J. Hirsch
*Attorney, Agent, or Firm*—Merchant, Gould, Smith, Edell, Welter & Schmidt

[57] ABSTRACT

A method and apparatus for catheterization is provided. The method and apparatus are particularly suited for bone catheterization, i.e. access to an internal cavity of an animal, by means of a bone associated therewith. The preferred apparatus includes a tap arrangement and a cannula arrangement, provided in fluid flow communication with one another. The tap arrangement is constructed and arranged for anchoring within a bone, in fluid flow communication with the cavity. The cannula is preferably oriented for fluid flow access therewith, from a remote location. In preferred applications, the cannula arrangement is provided in communication with a medical access port and/or infusion pump arrangement. A preferred tool is described, for implanting the apparatus in a bone of the subject.

4 Claims, 3 Drawing Sheets

METHOD AND APPARATUS FOR CATHETERIZATION

FIELD OF THE INVENTION

The present invention generally concerns catheterization. In particular, it concerns methods and apparatus for providing catheterization, through bone material, into cavities in animals, including humans. In preferred applications, catheterization is provided into joint cavities, for therapeutic treatment.

BACKGROUND OF THE INVENTION

For a variety of reasons, therapeutic access to internal cavities of animals, including humans, has been desirable. Herein the term "therapeutic access" will generally be understood to refer to access to the cavity from a remote location, for any of a variety of reasons. For example, the access may be desired in order to introduce therapeutic material into the cavity; in order to remove material from the cavity; and, in order to obtain access to the cavity with mechanical means such as an orthoscopic filament or laser surgery tool. The term "therapeutic access" is intended to include within its meaning access to treat conditions, study conditions, inhibit the onset of physical problems, etc.

There are a wide variety of reasons why access has been desirable, in both human and veterinary medicine. Herein the description will primarily focus on treatments of humans, and the focus of attention will be on joint cavities. Further, conditions of particular interest to the techniques and apparatus described herein are arthritic conditions; however it will be understood that: many of the methods and apparatus described herein may be applied to a wide variety of animals and not just humans; some of the techniques may be utilized for access to cavities other than joint cavities; and, some of the treatment methods described herein may be utilized for therapy other than treatment of arthritic conditions.

Again, a particular area in which the methods and apparatus described herein may be of use, is in the treatment of arthritis. More than 37 million individuals in the United States suffer from the broad category of joint diseases known collectively as arthritis. Among the more common of these conditions are: osteoarthritis, which is prevalent among elderly; and, rheumatoid arthritis, which tends to occur in relatively young men and women. When the pain associated with the conditions cannot be controlled by conservative treatments methods, and/or when function cannot be readily restored, joint replacement is often the presently prescribed treatment method. Approximately 120,000 hip replacements and 70,000 knee replacements are performed each year in the United States.

While joint replacement operations are generally successful for short term relief, loosening of implants and erosion of articulating surfaces pose problems over the long-term. As a result there have been ongoing efforts to improve joint prostheses. However, it is also desirable to develop treatment methodologies that avoid joint replacement or at least postpone its necessity.

Research has indicated that access to synovial fluid of a diseased joint could be a key factor in the development of new treatment methodologies. In particular, the nature of the synovial fluid has been linked to joint disease. A study of changes in the synovial fluid could provide information useful in long-term diagnoses and treatment and access to a joint for direct application of drugs and/or lubricants therein can lead to more effective modes of treatment for arthritic disease.

Cuevas et al., *Biochem. Biophys. Res. Comm.*, 156, 611 (1988), incorporated herein by reference, reported that administration of fibroblast growth factor directly into injured joints of rabbits for 20 days promoted repair of the damaged cartilage; while no evidence of damage repair was seen in control animals which received intra-articular saline infusions. Such studies support the contention that access to synovial fluid may be of considerable therapeutic value.

A typical conventional means of orthopedic joint access for fluid drainage and acute drug therapy has been by percutaneous hypodermic needle insertion. Studies during which artificial synovial fluid has been injected as an experimental treatment include the reports found in: Leardini et al., *Clinical Trials Journals*, Vol. 24, p. 341 (1987); Namiki et al., *International Journal of Clinical Pharmacology, Theory and Toxicology*. Vol. 20, p. 501 (1982); Grecomoro et al., *Phramatherapeutica*, Vol. 5., p. 137 (1987); and. Bragantini et al., *Clinical Trials Journal*, Vo. 25, p. 333 (1987). The previous four recited articles are incorporated herein by reference. In general, the articles report that one to three intra-articular injections per week of 20–40 mg (milligrams) of hyaluronic acid temporally relieved arthritis pain in some patients. However, two of the studies (Namikini et al. and Leardini et al.) report that the injections either produced pain lasting a few hours (3.3–4.7% incidence rate) or swelling which lasted a few days (1.0–2.5% incidence rate).

Besides the incidence of pain (and/or swelling) associated with treatment through use of hypodermic needles to provide percutaneous insertion, other potential problems and limitations are presented by this conventional technique. Examples of these are briefly discussed herein. The list is not intended to be considered as exhaustive.

If percutaneous hypodermic injection is to be utilized, then therapy extending over a substantial period of time would require subjecting the patient to a plurality of painful injections. This not only increases pain and discomfort to the patient, but also requires the patient to frequently return for treatment to a medical facility, increasing cost and inconvenience.

Another problem with this method of therapy is that treatment on a continuous basis, i.e. through continuous infusion, is not readily feasible. Further, the size of bolus which may be given in any given treatment will be severely limited by the size of the cavity and/or patient comfort.

Also, each injection may need to be precisely located, for maximum therapeutic effect. This may be difficult to achieve. The needle injection itself may cause damage, or provide a site of infection. For example, if the joint of concern is the knee joint, the cavity (or fluid containing capsule) is defined by bone structure and membrane. Generally, needle insertion would require piercing of the membrane. Thus, damage to the integrity of the capsule is involved, and infection may set in. The problem is exacerbated should a plurality of injections be necessary.

The studies of the four references discussed above were carried out on knee joints. Treatment of hip, wrist and finger joints would typically involve more technically difficult percutaneous needle puncture (in the case of the hip) or likely cause unacceptable trauma (in the case of the smaller wrist joint and tiny finger joints).

What has generally been needed has been a more convenient and effective method for obtaining therapeutic access to an internal cavity such as a joint cavity. Apparatus for conducting such methods have also been needed.

SUMMARY OF THE INVENTION

The present invention generally concerns methods and apparatus for therapy. The invention particularly concerns therapy for treatment of material in cavities in animals, including humans, wherein the cavity is an internal cavity at least partially defined by the surface of a bone in association therewith.

In certain preferred applications, the methods concern therapy for treatment of a bone joint in an animal, the bone joint having a cavity including fluid retained therein by means of a retaining membrane. This preferred application of the invention includes a step of selectively introducing therapeutic material into the cavity without piercing the retaining membrane. In preferred applications this is conducted by introducing therapeutic material into the cavity by means of delivering the therapeutic material through an access channel provided in a bone in contact with, or association with, the cavity. This may be done, for example, by drilling a hole through the bone, and introducing the therapeutic material therethrough. A preferred apparatus for introduction to the therapeutic material is described. In certain preferred methods, material introduced is selected from the group consisting of: hydrocortisone and related steroids; hyaluronic acid (lubricant); phenylbutazone; sodium salicylate; benzyl salicylate (anti-inflammatory agents); orgoteins; lidocaine (analgesics); fibroblast growth factor (growth factors) and, mixtures thereof.

A preferred embodiment of the present invention may be generally characterized as providing therapeutic access to an internal joint cavity of an animal, the cavity being defined at least in part by bone material. The preferred method generally includes steps of providing an access channel through the bone material defining the joint cavity, the access channel terminating in fluid flow communication with the cavity; and, providing fluid flow access with the access channel, from a remote location. As explained herein, the term "therapeutic access" in this context is meant to refer to access for any of a variety of reasons, not merely to introduce material into the cavity. For example, the access may be provided in order to remove material from the cavity, or in order to provide a preferred point of introduction of a mechanical device (or portion of a medical device) into the cavity. The term "therapeutic" in this context is meant to include access for any of a variety of means including treatment, inhibition of deterioration, investigation (examination) and/or experimentation.

It is further a method according to the present invention to provide selected therapeutic access to a cavity in an animal wherein the cavity is defined at least in part by bone surface, when the method is generally characterized by steps of: providing an access channel through a bone having a surface in association with the cavity, the access channel being provided in fluid flow communication with the cavity; securing a tap arrangement within the access channel, the tap arrangement having internal flow channel provided in fluid flow communication with the cavity; and, providing a cannula arrangement, or fluid flow arrangement with the tap arrangement internal flow channel. By this method, material can be inserted into or withdrawn from the cavity, by transport through the cannula arrangement and tap arrangement. In preferred applications, the tap arrangement will have been secured to the cannula arrangement prior to the insertion of the tap arrangement within the animal.

It is noted that the access channel may be provided simultaneously with the securing of the tap arrangement, for example if the tap arrangement is driven into the bone as a wedge, or drill bit.

Methods according to the present invention may be utilized to provide access to a variety of cavities, preferred applications being for treatment of arthritis for example in knee joint cavities, hip cavities and/or wrist and finger cavities.

In preferred applications, an infusion pump arrangement and/or medical access port are provided in fluid flow communication with the cannula arrangement, for medical access to the cavity. A variety of types of infusion pump arrangements and access ports may be utilized, and several are referenced herein, in the detailed descriptions. With such an arrangement selected control of material within the cavity is facilitated.

The present invention also includes within its scope the provision of an apparatus or arrangement for providing therapeutic access to a cavity in an animal, for example a human, when the cavity is defined, at least in part, by a surface of a bone adjacent the cavity. The preferred apparatus generally comprises: an implantable (biologically compatible) tap arrangement constructed and arranged for anchoring in the bone; and, a cannula arrangement secured to the tap arrangement and having an external conduit in fluid flow communication with the tap arrangement. Preferably, the tap arrangement has an internal longitudinal channel extending therethrough, and the cannula arrangement includes an end extension positioned within the tap arrangement longitudinal channel. For preferred applications, the tap arrangement comprises a screw-like construction, having a threaded shank portion for anchoring in the bone. Alternate arrangements, however, may be utilized.

Preferably the cannula arrangement comprises an implantable (biologically compatible) flexible conduit, that can be readily secured subcutaneously in the subject. This will provide for ease of movement, and more efficient operation.

A preferred tool for implanting preferred apparatus according to the present invention is also provided. The tool generally includes a shank portion having an end adapted for secure mating with a portion of the tap arrangement; and, a longitudinal slot for receipt of the cannula arrangement therein. Preferably the tool includes means for secure gripping thereof, for example a handle portion. Herein the apparatus is generally referred to, in some instances, as a "bone catheter" for convenience.

Another application of the invention will be apparent from the detailed descriptions. In particular, the tap arrangement may be provided in communication with an interior of a bone, rather than a natural cavity. Thus, therapeutic access to a bone interior can be provided.

BRIEF DESCRIPTION OF THE DRAWINGS

The drawings constitute a part of the specification and include exemplary embodiments of the methods, techniques and apparatus disclosed herein. The drawings are meant to be exemplary only, and not otherwise limiting. It will be understood that in some instances relative material thicknesses, and component sizes, may be shown exaggerated to facilitate understanding.

DETAILED DESCRIPTION OF THE INVENTION

As required, detailed descriptions of methods, techniques and apparatus of the invention are presented herein. The descriptions are intended to be exemplary only, and to provide support for the general methods and apparatus claimed. The descriptions are not intended to be limiting, but rather as a basis for support of the claims.

In general, the methods of the present invention concern providing therapeutic access to an internal cavity of an animal, including humans, wherein that cavity is defined at least in part by a bone surface; that is wherein the cavity is adjacent a bone. In general, the method concerns obtaining access to the cavity in a manner which does not involve undesirable piercing or rupture of a membrane associated with enclosing the cavity (if there is one). The method generally comprises providing an access channel through a bone in contact with the cavity, the access channel terminating in fluid flow communication with the cavity; and, delivering the therapeutic material into the cavity by transport through the access channel. Specific details concerning the applications and the methods, and the particular therapeutic agents that may be introduced into the cavity, are described hereinbelow. First, the apparatus will be generally described.

PREFERRED APPARATUS FOR USE IN METHODS ACCORDING TO THE PRESENT INVENTION

For purposes of facilitating understanding of the apparatus, it will be described herein as applied in association with a human knee. More general applications, at other body cavities in humans, and other animals, will be apparent from the description. As previously indicated, the apparatus may be anchored for access to an interior of a bone, rather than a cavity.

In general there are a variety of reasons why therapeutic access to such a cavity may be desired; and, the term "therapeutic access" is meant to include any of a variety of reasons for such access. For example, the term is intended to include within its scope: access in order to deliver therapeutic material or agent to the cavity; access in order to remove material from the cavity; and, access in order to provide a mechanical means such as orthoscopic filament and/or surgical fiber into the cavity. The term "therapeutic" and variants thereof in this context is meant to include access for treatment, examination and/or experimentation. Herein, for simplicity, description will generally focus on examples involving introduction of material to the cavity or removal of material from the cavity.

Figure 1:
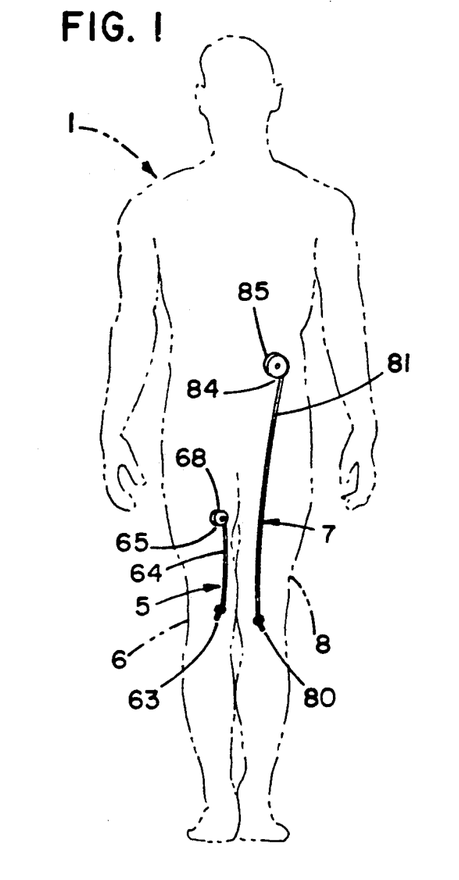
FIG. 1 is a schematic perspective view of a subject of the methods of the present invention.

In the schematic of FIG. 1, a subject 1 (in phantom) is depicted having a first apparatus 5 according to the present invention provided in communication with his right knee 6; and, a second apparatus 7 according to the present invention implanted for communication with his left knee 8. Herein, apparatus such as 5 and 7 will sometimes be referred to as "orthopedic catheters" or "bone catheters". In general, differences between the system involving apparatus 5 and the system involving apparatus 7 relate to means provided for access to an anchored end of the apparatus, and therapy. These will be discussed in more detail hereinbelow. Initially, however, detailed descriptions with respect to those features concerning apparatus 5 and 7 that are similar are presented. With respect to this, attention is directed to FIG. 2.

Figure 2:
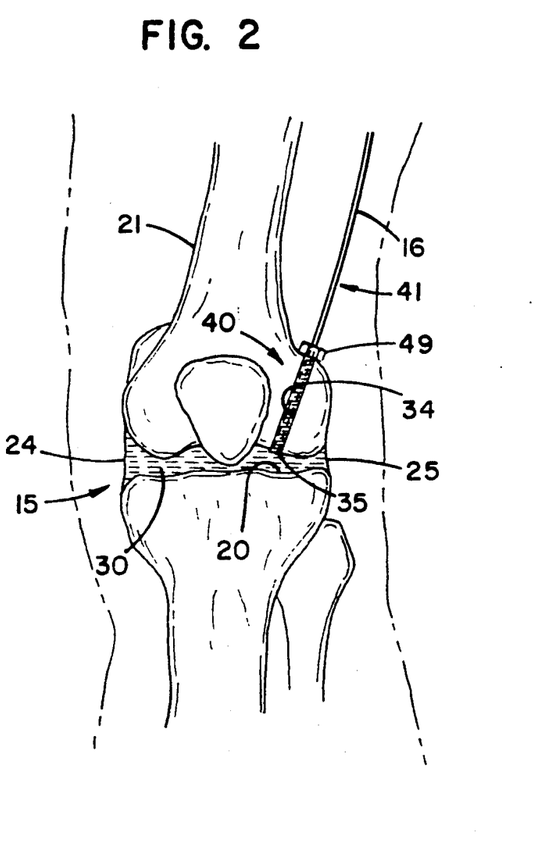
FIG. 2 is an enlarged fragmentary schematic view of a joint in an animal treated according to the methods of the present invention.

In FIG. 2, a schematic representation of bone joint 15 treatable according to the methods of the present invention, with apparatus of the present invention, is illustrated. In FIG. 2, joint 15 is shown provided with an apparatus 16 according to the present invention. The apparatus 16 of FIG. 2 may correspond to either of apparatus 5 and 7, FIG. 1 (in phantom). The joint 15 of FIG. 2 may be a human knee joint, as depicted in FIG. 1. However, it may be another type of joint such as a hip joint, wrist joint, finger joint, etc.; and, it may be a joint of an animal other than a human. More generally, the cavity being treated may be a joint cavity, as shown; however, it may be another type of internal cavity adjacent a bone.

Referring to FIG. 2, joint 15 comprises a joint cavity 20, defined by bones 21 and 22. The cavity is further defined by membrane or membrane surfaces 24 and 25 attached to the bones, and enclosing cavity 20. The enclosed cavity 20 may be referred to as the joint capsule.

It will be understood that the schematic of FIG. 2 is highly simplified, relative to the actual depiction of a joint. Ligaments, etc. for example, are not depicted. Also, precise relative size of depicted components is not indicated. In general, cavity 20 defined by membrane sections 24 and 25 and surfaces of bones 21 and 22 includes therein synovial fluid 30. As previously discussed in the background section, conditions involving deterioration of joint operation have been, in some instances, linked to the nature of, or condition of, the synovial fluid 30.

According to the present invention, therapeutic access is provided to cavity 20 by means of a preferred apparatus 16. More specifically, a bore or channel 34 is provided in a bone associated with a cavity 20, for the illustration of FIG. 2, bone 21. Channel 34 is driven through bone 21, and terminates at opening 35 in fluid flow communication with capsule 20. It will be understood that therapeutic access to cavity 20, therefore, is provided by means of channel 34 and opening 35. This access is provided without piercing of membrane sections 24 and 25, since the access generally comprises a bore driven directly through one of the bones, i.e. bone 21. The precise, preferred, location of the bore will depend upon the particular cavity involved, the nature of the adjacent bones, and the preference of the surgeon. A wide variety is possible.

According to the invention, therapeutic access through channel 34 is preferably provided by means of apparatus 16. Apparatus 16 includes two principal components comprising: a tap arrangement 40; and, a conduit or cannula arrangement 41. Tap arrangement 40 provides means for by which cannula arrangement 41 is anchored in fluid flow communication with cavity 20, i.e. in channel 34. Apparatus 16 will be better understood by reference to FIG. 3.

Figure 3:
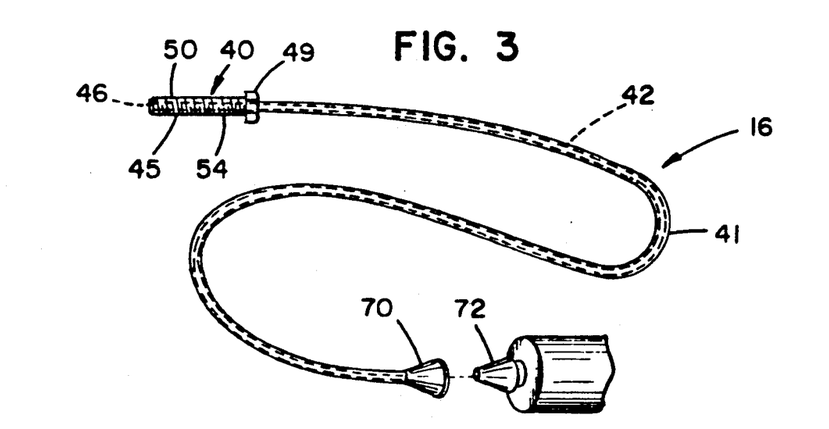
FIG. 3 is a perspective view of an apparatus according to the present invention.

Referring to FIG. 3, apparatus 16 depicted therein, in perspective, includes tap arrangement 40 and cannula arrangement 41. Preferably cannula arrangement 41 comprises an elongate flexible cannula having an internal lumen, bore or flow through channel 42, extending longitudinally therethrough. While a variety of materials may be utilized for cannula arrangement 41, preferably the arrangement comprises a flexible conduit of biologically compatible material such as silicone rubber or polyurethane/silicone rubber copolymer. Such materials are available for example under the designation SILASTIC Tubing from Dow Corning, and MOxMed of Portage, Wis. The tap arrangement 40 generally provides for anchoring of cannula arrangement 41, in fluid flow communication with the cavity or capsule. The term "tap" in this context is not meant to indicate any particular direction of fluid flow.

Tap arrangement 40 includes means for anchoring within a bone, and in particular within a channel formed in the bone, as described above with respect to FIG. 2. For the preferred arrangement of FIG. 3, tap arrangement 40 comprises a hollow screw member 45 having a longitudinal channel 46 (FIG. 5) extending therethrough. Screw member 45 generally comprises a head portion 49, and a shank portion 50. The shank portion 50 is provided with external threads 51 for use in anchoring tap arrangement 40 to a bone, for example, as shown in FIG. 2 to an internal surface of bore or channel 34. For the preferred embodiment shown, FIG. 3, shank portion 50 is threaded throughout its entire length.

Figure 4:
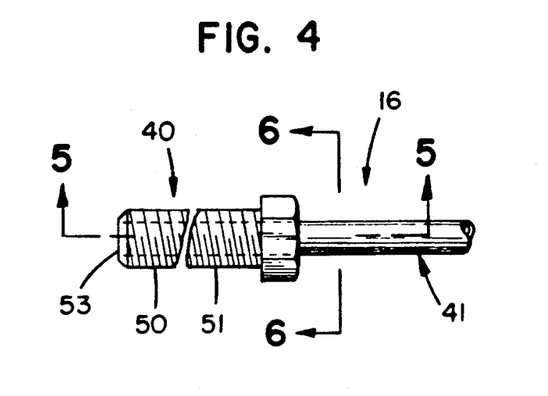
FIG. 4 is an enlarged fragmentary view of a portion of the apparatus shown in FIG. 3.
Figure 5:
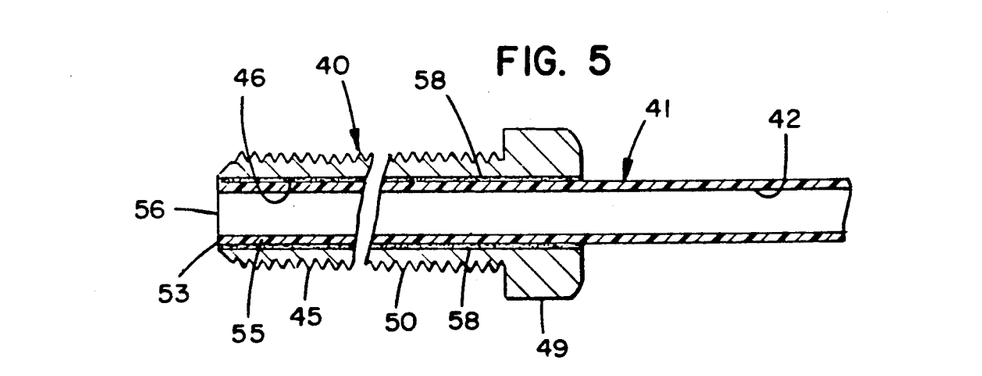
FIG. 5 is a cross-sectional view of a portion of the apparatus shown in FIG. 4, the cross-section being taken generally along line 5—5, FIG. 4.

Attention is now directed to FIGS. 4 and 5, wherein tap arrangement 40 is shown in greater detail. Referring to FIG. 4, cannula arrangement 41 is shown in fluid flow communication with internal bore 46 of tap arrangement 40. Thus, the internal channel of cannula 41 communicates through tap arrangement 40, to tip 53 thereof. Referring to FIG. 5, for the preferred embodiment, an extension 55 of cannula arrangement 41 is threaded (i.e. projects) completely through channel 46 of screw member 45, so that an end 56 of cannula arrangement 41 is adjacent or substantially flush with end 53 of screw member 45. In preferred embodiments this arrangement is provided, since in general for presently available materials, silicone rubber or the like from which cannula arrangement 41 is preferably formed tends to be non-thrombogenic, to a greater extent than preferred, relatively rigid, materials from which screw arrangements such as screw member 45 would be formed. Providing the soft, flexible, biologically compatible silicone rubber type material in the vicinity of end 53 will thus tend to inhibit closing or blocking thereof, or overgrowth. It will be understood, however, that a wide variety of arrangements may be utilized.

For the preferred arrangement shown in FIG. 5, extension 55 of cannula arrangement 41 is shown secured to tap arrangement 40 by means of adhesive layer 58. A variety of biologically compatible, and relatively stable, adhesives, may be utilized including an implant grade room temperature vulcanizing silicone rubber adhesive, such as available from Dow Corning as a medical SILASTIC elastomer. Alternate methods of securing may also be used.

Operation of apparatus 16 will be further understood by reference to FIG. 2. Screw member 45 is shown driven into bore 34. By means of cannula arrangement 41, fluid flow communication with cavity 20 (i.e. therapeutic access to cavity 20) is provided. Preferably, screw member 45 is driven far enough so that it projects beyond a surface of bone 22, at port 35, a sufficient distance to inhibit bone overgrowth, but not so far as to inhibit joint operation; for example, it should not contact or interfere with the moving condyle surfaces. In some applications, not shown, a "head" of the top arrangement may be countersunk.

Preferred manners in which an arrangement similar to arrangement 16 may be utilized, will be further understood by reference back to FIG. 1. In the right leg of the subject shown in FIG. 1, apparatus 5 is shown anchored by means of tap arrangement 63 in the right knee 6 of the subject 1. It will be understood that tap arrangement 63 will have been positioned, for fluid flow communication with the joint cavity. Apparatus 5 includes a cannula arrangement 64 in fluid flow communication with tap arrangement 63, and hence the cavity. Cannula arrangement 64 may be as previously described, and will preferably have been surgically positioned subcutaneously, i.e. under the skin of subject 1. The cannula arrangement includes an end 65, remote from tap arrangement 63. End 65 is adapted for access by a medical technician (or others) to ultimately obtain therapeutic access to the cavity at tap arrangement 63.

For the arrangement shown in FIG. 1, end 65 is attached to a medical access port or port arrangement 68 which terminates at a selected location for access. It will be understood that in a variety of manners, means may be attached to (or provided in association with) access port 68 for convenient therapeutic access to the cavity in fluid flow communication with the tap arrangement 63. For example aspiration means may be attached to (or coupled with) the port 68, to aspirate or remove fluid from the remote cavity. Alternatively, fluid infusion means may be attached to (or coupled with) port 68, to inject or infuse material into the cavity. Devices for irrigation of the cavity may be used. It will also be seen that cannula arrangement 64 provides a convenient physical passageway, directed into the remote cavity, so that the end of an object such as a needle, fiber optic or laser surgery optic could, if desired, be readily directed into the cavity by means of the cannula arrangement 64.

A wide variety of medical access ports that could be adapted for use in applications described herein are known. The various types include: single lumen bolus injection ports; multi-lumen bolus injection ports; and, multi-catheter bolus injection ports. Included among commercially available ports are the Port-A-Cath available from Pharmacia Deltec of St. Paul, Minn.; I NFUEE-A-PORT, available from Shiley Infusaid (Pfizer), Norwood, Mass.; and, LifePort, available from Strato Medical of Beverly, Mass. These and other conventional ports, or ports yet to be developed, may be utilized with apparatus according to the present invention. In general, the various ports will have a variety of means for attachment to a lumen or cannula arrangement, such as cannula arrangement 64. It will be understood that the end 65 of cannula arrangement 64 will be selected so as to be adapted for the particular connection to be made. An example of this is illustrated in FIG. 3, whereat end 70 is adapted for secure to male connector 72. A variety of means may be utilized to provide for secure attachment including: a suture-type connection; a restrictive elastic portion in end 70; adhesives; male./female connectors, etc.

In some applications it may be preferable to provide apparatus according to the present invention in fluid flow communication with an implanted pump. An example of this is illustrated in FIG. 1 with respect to apparatus 7. Apparatus 7 includes a tap arrangement 80 anchored within a bone of knee 8, for fluid flow communication with a joint cavity or capsule thereat. Apparatus 7 includes cannula arrangement 81 in fluid flow communication with tap arrangement 80, and thus the associated cavity. The tap arrangement 80 and cannula arrangement 81 of apparatus 7 may be as previously described.

For arrangement 7, cannula arrangement 81 is shown having remote end 84 provided in fluid flow communication with pump arrangement 85. The pump arrangement 85 is shown surgically implanted at the abdomen of subject 1. Pump arrangement 85 may be utilized to preferably deliver therapeutic material through cannula arrangement 81 into the cavity at the knee, in a variety of manners. For example, it may be provided with means for continuous infusion or selected infusion at intermittent intervals.

A variety of pump arrangements may be utilized as arrangement 85. These would include electronically programmable pump arrangements and single infusion rate pumps. It should also be apparent that pump-port combinations may also be used.

Some pump arrangements readily adaptable for use in systems according to the present invention are commercially available. Included among these are the Infusaid pump available from Shiley (Pfizer), Norwood, Mass.; the SynchroMed pump available from Medtronic, Minneapolis, Minn. Other pumps utilizable in systems according to the present invention include the spring pumps of U.S. Pat. Nos. 4,718,893 and 4,772,263, incorporated herein by reference.

As previously suggested with respect to ports, a variety of proximal end fittings in end 84 of cannula arrangement 81 may be utilized, for adaptation in connection to a variety of pump arrangements. Connection means, for example, such as suture connections, adhesives, restrictive elastic materials and/or male/female interlocking connectors may be utilized.

Referring again to FIG. 4, tap arrangement 40 may be manufactured from a variety of materials. In general what is required is: a material which is biologically compatible and implantable; and, a material which is relatively rigid and thus anchorable in a manner insuring connection without likely collapse or plugging of the channel end cannula 41. It is foreseen that among the more desirable materials for use in preparing tap arrangement 40 are materials from which conventional bone screws are preferably made, for example titanium and stainless steel. Other materials which may be utilized include: various plastics; various other metals and metal alloys; and, ceramics.

For the arrangement shown in FIGS. 1-6, the tap arrangements have been illustrated with a threaded shank, for anchoring via screwing into a channel in the bone. Other means for securing the tap arrangement in place may be utilized including: wedge arrangements, adhesives and the like. In general, what is required is a secure anchor, to protect against problems from the arrangement coming loose or unsecured. An advantage to the threaded arrangements shown is that they may be readily removed, should bone overgrowth justify redrilling a portion of the bone.

The specific dimensions of components of an arrangement according to the present invention will depend, of course, upon the particular application. The arrangement utilized in the experiments described herein, and generally utilizable in a human knee, include a tap arrangement having: a shank diameter of about 0.3-0.6 cm; an overall length of about 1.0-4.0 cm; and, an internal bore of about 0.05-0.2 cm. The length of the cannula arrangement will depend upon the selected preferred location for the distal end, for example the location of the port and/or pump. It is foreseen that apparatus according to the present invention may be miniaturized, for use in wrist or finger joints.

Figure 8:
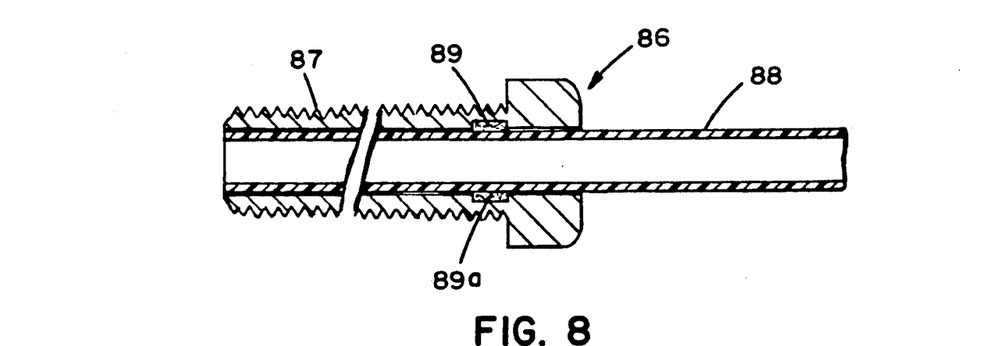
FIG. 8 is a fragmentary cross-sectional view of an alternate arrangement of the present invention, FIG. 8 being generally analogous to the view of FIG. 5.

Referring to FIG. 8, an alternate arrangement for anchoring the cannula within the tap arrangement is provided. Referring to FIG. 8, an apparatus 86 is depicted in cross-section, comprising tap arrangement 87 and cannula arrangement 88. These are generally as previously described, except tap arrangement 87 includes an internal recess 89 therein filled with adhesive material 89a. The adhesive material 89a may be set, after cannula 88 is put in place, to facilitate anchoring of cannula arrangement 88 within tap arrangement 87.

It will be understood that the ends of arrangements according to the present invention, for example tips 53 and 56, FIG. 5, may be provided with a variety of designs. It is foreseen that specific shapes, etc. may be preferred, to: provide for lack of irritation to the patient or material within an associated capsule; to inhibit likelihood of blockage through bone overgrowth or clotting, etc.; and/or to facilitate anchoring in position. The arrangements illustrated in FIGS. 5 and 8 are intended to be exemplary only, with respect to this.

Methods for Securing Systems According to the Present Invention in Place

A variety of surgical methods may be utilized to put apparatus according to the present invention in place. In general preferred methods involve a step of providing a bore or channel in a bone, for securing the tap arrangement. Typically this will involve drilling a bore or channel through the bone, to provide a channel having an end in fluid flow communication with the cavity of interest. A variety of conventional bone drilling apparatus, or means yet to be developed, may be utilized for this process.

A follow up step of the preferred process will involve anchoring the tap arrangement in place, for example by driving (i.e. threading) the shank of an apparatus as shown in FIG. 4, into the bore. A wrench or the like may be utilized to provide the arrangement. In preferred applications, the flexible cannula arrangement will have been attached to the tap arrangement prior to the step of anchoring the tap arrangement in the bore.

To facilitate anchoring of the tap arrangement under such circumstances, a preferred wrench arrangement is provided. The preferred wrench arrangement is illustrated in FIG. 7.

Figure 6:
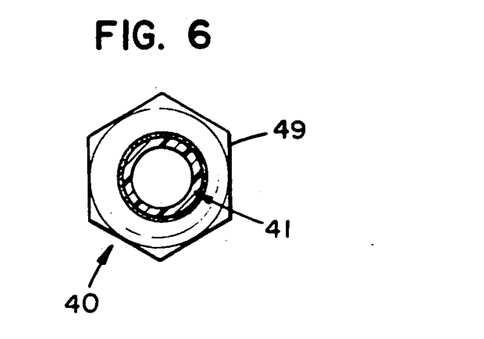
FIG. 6 is a cross-sectional view taken generally along line 6—6, FIG. 4.
Figure 7:
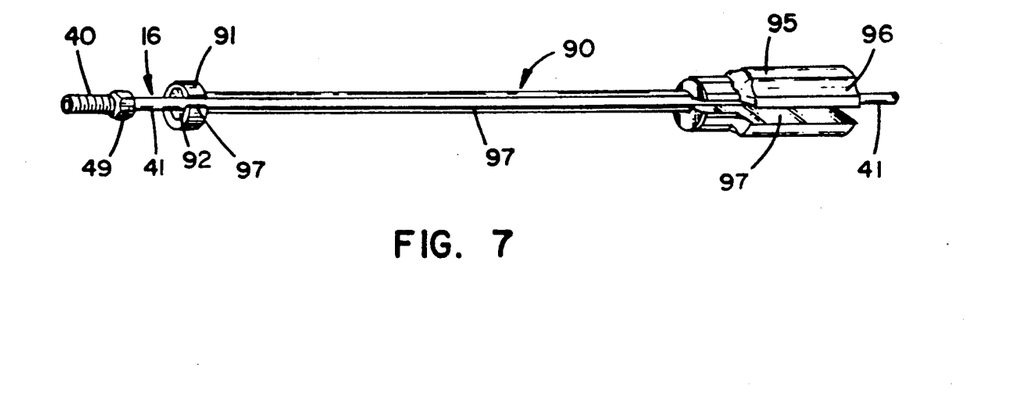
FIG. 7 is a perspective view of a combination catheter apparatus according to the present invention and device for use in mounting the catheter apparatus in a subject, according to methods of the present invention.

Referring to FIG. 7, wrench arrangement 90 is depicted. The arrangement includes a first end 91 adapted for secure engagement with a tap arrangement, such as tap arrangement 40 of apparatus 16. Tap arrangement 40 includes a head portion 49 of a shape for engagement by a wrench or the like. End 91 of wrench 90 includes recess 92 therein sized for mating with head 49. For example, head 49 may be provided with a hexagonal shape, engageable by a mating hexagonal recess in wrench 91. Referring to FIG. 6, such a hexagonal shape to head 49 is illustrated.

Wrench 90 is provided with a handle section 95 which may be readily gripped by a user, to drive or wrench tap arrangement 45 into position. Handle 95 is provided with ribs 96 and the like, to facilitate gripping thereof.

Wrench arrangement 90 is provided with an elongate slot 97 therein extending completely longitudinally therealong. Slot 97 is adapted for receipt of tube or cannula arrangement 41 therein, when tap arrangement 45 is engaged. Thus, tap arrangement 45 can be readily rotated, without problems from interference by cannula 41. After the process of anchoring tap arrangement 45 is completed, wrench 90 can be readily removed by sliding cannula arrangement 41 out of slot 97.

In general, operations involving assemblies according to the present invention will include performing the surgery in a manner to provide for subcutaneous passage of the cannula arrangement 41 to a selected remote area, such as an area of positioning an access port or pump. The method may also include securing the access port or pump to the patient, in an appropriate location; and, connecting, in a fluid flow manner, the cannula arrangement thereto.

It is noted that the methods previously described generally involve anchoring by means of threads or the like. Alternate anchoring, including wedge arrangements, adhesives or similar anchoring methods, may be utilized. In general, the processes will be as described, except modified to accommodate the different anchoring means and/or methods. In some applications the tap arrangement may be driven as a wedge into the bone, without a preformed bore, thus forming the bone simultaneously with the anchoring.

Preferably anchoring is done such as to inhibit the likelihood of formation of a sharp bend or crimp in the cannula arrangement. Referring to FIG. 2, for example, this is accomplished by positioning the screw head 49 such that as the cannula extends outwardly therefrom no sharp turn is required.

Methods of Treatment

A variety of drugs have been given intraarticularly by percutaneous needle puncture of a joint. It is foreseen that such drugs may be beneficial if introduced according to the methods of the present invention, i.e. through an anchored catheter arrangement as described.

It is foreseen that the methods of the present invention may be utilized to deliver a variety of types of drugs to the cavity, for example: steroids; analgesics; anti-inflammatory agents; growth factors; lubricants; orgoteins; and, mixtures thereof. Specific examples of such drugs include: hydrocortisone; hyaluronic acid; phenylbutazone; sodium salicylate; benzyl salicylate; orgotein; lidocaine; and, fibroblast growth factor. Advantages from utilization of systems according to the present invention are numerous. For example, the volume of the synovial space is small (approximately 4 cubic centimeters in the human knee), in the past limiting bolus therapy to applications in which the drug can be at a relatively high concentration. Also in the past bolus therapy has been limited to drugs in which the biological effect following injection is relatively long, due to the undesirability of repeated injections. Considering these two factors, along with the chronic nature of the disease state, it is expected that therapies according to the present invention, particularly those involving continuous drug infusion (or frequent intermittent infusion) by implantable pump will be advantageous. The orthopedic catheters described above will, for example, generally facilitate the development of treatment modes in which the concentration of a drug or combinations of drugs within a joint space is maintained at a prescribed, optimal, level.

In addition to routine clinical application, arrangements and methods according to the present invention will be useful in aiding research on joint disease. For example, once the arrangement is in place it may be utilized to draw fluid samples from the cavity, for study.

The thin membrane that retains the synovial fluid within the joint space is relatively fragile. It is in general preferred to avoid rupture or tearing of this tissue. Preferred methods described herein involve anchoring of the catheter in place without undesired disruption of the membrane. Further, access to the enclosed capsule or cavity is provided, again without substantial disruption of the membrane, to advantage. For example, in the knee joint the enlarged bone end of the femur provides an entrance point for a bone catheter that enters the joint capsule in an area where there is no contact between the bones during normal movements. This can be done in a manner avoiding the terminal points of the ligaments, to advantage.

It is foreseen that arrangements according to the present invention may be utilized in cavities or capsules other than joint cavities. For example, they may be anchored in the skull, for use in obtaining access to cerebral spinal fluid. They may also be provided in a manner terminating within a bone, rather than a natural cavity, to provide therapeutic access thereto. In general, the techniques will be as previously described, and the apparatus may be as discussed, except modified as necessary, for example, in size, to accommodate the application.

If the therapy involves injection of material, rate of injection will generally be dictated by therapeutic needs. However, flow of material outwardly by means of injection into the capsule can be utilized to facilitate long-term operation by inhibiting blockage due to bone overgrowth and/or clotting. This can be facilitated by utilizing a cannula arrangement with a particularly small internal diameter, since the smaller internal diameter will dictate a higher end pressure, for a given flow rate measured as volume of fluid passing outwardly therefrom per unit time. Other means to facilitate maintenance of good fluid flow may include physical and/or chemical cleaning; that is cleaning by inserting a snake through the cannula arrangement, or inserting biologically compatible chemical cleaners therethrough.

EXPERIMENTAL EXAMPLES

A characteristic of degenerative joint disease is a slow destruction of the synovial cells, which secrete a joint lubricating glycoprotein complex (an important component of which is hyaluronic acid). With this dysfunction, movement of the joint becomes painful, victims less active, and degeneration progresses since, in part, joint activity appears to promote synovial cell function. One therapy involves simply forcing continued activity, even if painful, in order to maintain the viability of the remaining cells. At least theoretically if the diseased joint were lubricated, movement would be less painful and patients would naturally resume previous levels of activity. Two animal models, of this type of therapy, were developed. In one model, a joint access catheter was attached to a bolus injection port, and in the other model the catheter was attached to a continuous infusion pump.

Experiment 1: in vivo port application

Two Canine hindlimb knee joints were injected twice weekly with 1.5 ml of 2.5 mg/ml solutions of hyaluronic acid for eight weeks, via a bone anchored orthopedic catheter arrangement, generally as described above, attached to a subcutaneously placed bolus injection port. The bolus injection port was located in the iliac fossa, approximately 12 inches away from the joint space. A control animal was provided with the device, and received twice weekly injections of bacteriostatic saline, for five months. Forty control and thirty-two experimental injections were provided, in the absence of anesthesia or tranquilizers. The animals did not exhibit symptoms of discomfort. No evidence of joint degradation was found at post mortem examination.

Example 2: in vivo pump application

Using a process similar to that described with respect to Example 1, a fourth dog was implanted. This time the orthopedic catheter was attached to an implanted hyaluronic acid infusion pump located approximately 23 inches away from the knee joint, in the shoulder fossa. Hyaluronic acid was injected via the infusion pump, and the rate of infusion was examined.

In order to establish operation of the infusion pump and catheter system, it was operated in vitro, in a pre-implant body temperature incubator (at 37° C.), for a period of time prior to insertion in the animal. After insertion in the animal, flow rate, i.e. rate of infusion, was also examined.

Figure 9:
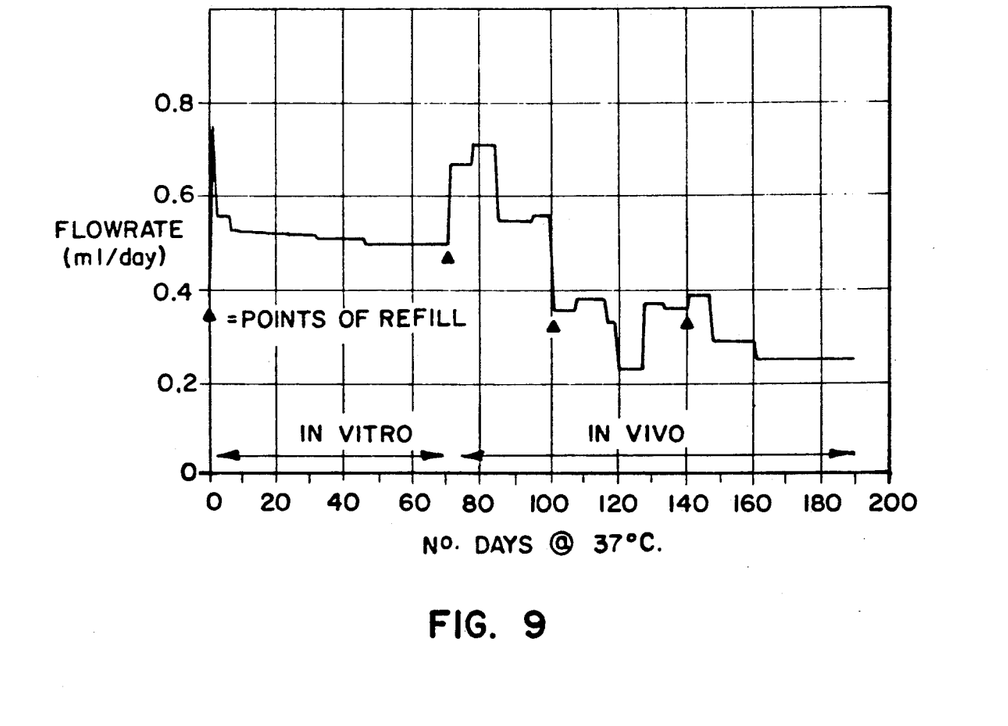
FIG. 9 is a graph representing data derived from an experiment described herein.

In FIG. 9 a plot of flow rate (ml per day) versus passage of time is presented both for the period of in vitro (incubation) study and in vivo study. The graph indicates that continual infusion can be readily obtained with apparatus and methods according to the present invention. With respect to the graph it is noted that the infusion pump utilized was very sensitive, with respect to flow rate, to changes in viscosity of the solutions therein. Viscosity fluctuations, and thus flow rate fluctuations, sometimes resulted when, for example, dilution or similar changes in concentrations of the injected fluid changed. In the figure, the arrow heads indicate times at which the pump was refilled.

From the above experiments, it can be concluded that maintenance of adequate drug levels can be readily achieved over at least several month pump refill interval. Compared to one to three bolus injections per week, this represents a great reduction in trauma to the patient and considerable savings.

What is claimed is:

1. A therapeutic apparatus comprising:
   (a) an implantable tap arrangement constructed and arranged for anchoring in a bone; said tap arrangement having a head portion and a shank portion, said head portion and shank portion being adapted for implantation completely internally of a patient;
      (i) said head portion and shank portion having a longitudinal channel extending completely therethrough;
   (b) a cannula arrangement comprising an implantable flexible conduit having an internal conduit extending therethrough; said conduit including an end extension positioned within, and in extension completely through, said longitudinal channel in said tap arrangement; said conduit extension end portion comprising flexible, biologically compatible material and being resistant to bone overgrowth.

2. An apparatus according to claim 1 wherein:
   (a) said flexible conduit includes an end portion remote from said tap arrangement; and,
   (b) said apparatus includes a medical access port in fluid flow communication with said conduit end portion remote from said tap arrangement; said medical access port being constructed and arranged for mounting on the body of a patient.

3. An apparatus according to claim 1 wherein said flexible, biologically compatible material is a silicone rubber material.

4. An apparatus according to claim 1 wherein:
   (a) said flexible conduit includes an end portion remote from said tap arrangement; and,
   (b) said apparatus includes an infusion pump in fluid flow communication with said cannula arrangement end portion remote from said top arrangement.

* * * * *

UNITED STATES PATENT AND TRADEMARK OFFICE
CERTIFICATE OF CORRECTION

PATENT NO. : 5,120,312

DATED : June 9, 1992

INVENTOR(S) : Bruce D. Wigness et al.

It is certified that error appears in the above-identified patent and that said Letters Patent is hereby corrected as shown below:

Column 4, line 1 "or" should read --in--.

Column 7, line 29 "MOxMed" should read --Mox Med--.

Column 14, line 51 "top" should read --tap--.

Signed and Sealed this

Twenty-sixth Day of October, 1993

Attest:

BRUCE LEHMAN

Attesting Officer

Commissioner of Patents and Trademarks